United States Patent
Yasue

(10) Patent No.: US 6,547,718 B1
(45) Date of Patent: Apr. 15, 2003

(54) SEXUALLY SENSITIVE PORTION STIMULATING RING AND STORING DEVICE THEREFOR

(75) Inventor: Nobuhiro Yasue, Nakatsugawa (JP)

(73) Assignee: Toukaigikenkougyo Corporation, Nakatsugawa (JP)

( * ) Notice: Subject to any disclaimer, the term of this patent is extended or adjusted under 35 U.S.C. 154(b) by 0 days.

(21) Appl. No.: 09/807,433

(22) PCT Filed: Oct. 20, 1999

(86) PCT No.: PCT/JP99/05780

§ 371 (c)(1),
(2), (4) Date: Apr. 19, 2001

(87) PCT Pub. No.: WO00/27319

PCT Pub. Date: May 18, 2000

(30) Foreign Application Priority Data

Nov. 9, 1998 (JP) .......................... 10-317310
Jul. 12, 1999 (JP) .......................... 11-197758

(51) Int. Cl.[7] .................................................. A61F 5/00
(52) U.S. Cl. ...................................................... 600/38
(58) Field of Search .................................... 600/38–41

(56) References Cited

U.S. PATENT DOCUMENTS 3,495,589 A * 2/1970 Clement ...................... 600/38
4,203,432 A * 5/1980 Koch ........................... 600/41
D343,246 S * 1/1994 Gaylor et al. ............... D24/143
D431,865 S * 10/2000 Norton et al. ............... D24/143
6,193,753 B1 * 2/2001 Nordheim et al. ............ 600/38
6,231,502 B1 * 5/2001 McCarty ....................... 600/38
6,319,194 B1 * 11/2001 Wulf ............................ 600/41

FOREIGN PATENT DOCUMENTS

| JP | 54-81697 | 6/1979 |
| JP | 57-64350 | 4/1982 |
| JP | 3-149043 | 6/1991 |
| JP | 5-11935 | 2/1993 |
| JP | 6-57326 | 8/1994 |
| JP | 10-314205 | 12/1998 |

* cited by examiner

*Primary Examiner*—Samuel G. Gilbert
(74) *Attorney, Agent, or Firm*—Law Offices of David G. Posz

(57) ABSTRACT

A sexual stimulation device is placed on the root of the penis before sexual intercourse and is constructed of an outer ring and an inner ring. During sexual intercourse a first portion of the inner ring is displaced inwardly, resulting in a squeezing force being applied to the root of the penis and a second portion of the inner ring and a portion of the outer ring are displaced outwardly and contact the vulva of the female sex organ.

23 Claims, 14 Drawing Sheets

(a)

(b)

(c)

(a)

(b)

SEXUALLY SENSITIVE PORTION STIMULATING RING AND STORING DEVICE THEREFOR

TECHNICAL FIELD

The present invention relates to a ring-shaped sexually sensitive portion stimulating tool which is fitted on a penis root and an accommodating device therefor.

BACKGROUND ART

A large number of annular sexually sensitive portion stimulating rings, mounted on the root of a male penis for inducing erection of the male penis and keeping the male penis erected have been developed. These tools are intended to maintain an erected state by squeezing the root of the male penis.

A penis erection inducing tool disclosed in Japanese Utility Model Application Laid-Open No. 5-11935 is a representation of these sexually sensitive portion stimulating rings. In the penis erection inducing tool, a plurality of annular squeezing tools are mounted on the root of the penis in such a way that the one having a small diameter is mounted on the rear side of the penis root, whereas the one having a large diameter is mounted on the front side thereof to induce erection of the penis and maintain an erected state.

However, the above-described conventional tool is intended to stimulate the male penis but not intended to stimulate the female sexual organ.

DISCLOSURE OF THE INVENTION

The present invention has been made in view of the above-described situation. Therefore, it is an object of the present invention to provide a sexually sensitive portion stimulating ring capable of giving a female a feeling of sexual pleasure by stimulating a female sexual organ during sexual intercourse.

To achieve this object, the present invention has the characteristics described in each item of the scope of claims.

Specifically, in the invention described in claim 1, there is provided a ring-shaped sexually sensitive portion stimulating tool including an elastically deformable ring body, a first displacement portion which is provided on the ring body and is elastically displaced to an inner side in a widthwise direction of the ring body when the ring body is pressed in the widthwise direction of the ring body, and a second displacement portion which is provided on the ring body and is displaced to an outer side in the widthwise direction of the ring body with a displacement of the first displacement portion to the inner side in the widthwise direction of the ring body. The second displacement portion is constructed as a female sexual organ stimulating portion.

Owing to the above-described construction, with the displacement of the first displacement portion to the inner side in the widthwise direction of the ring, the second displacement portion serving as the female sexual organ stimulating portion displaces to the outer side in the widthwise direction of the ring. Therefore, during sexual intercourse, it is possible to give a feeling of sexual pleasure to a female.

In this case, according to the invention specified in claim 2, the second displacement portion makes an outward displacing motion in the widthwise direction of the ring body while the second displacement portion is displaced outwardly in a radial direction of the ring body. According to the invention specified in claim 3, a peripheral portion of the second displacement portion makes an outwardly spreading motion in the widthwise direction of the ring body, with an inner peripheral portion of the second displacement portion in the radial direction of the ring body serving as a supporting point.

In the invention described in claim 4, there is provided a ring-shaped sexually sensitive portion stimulating tool including a ring body that is elastically deformable. The ring body has an inner ring, approximately U-shaped in section, having a groove open in a peripheral direction thereof; and an outer ring which has a female sexual organ stimulating portion and is fitted in the groove of the inner ring. When the inner ring deforms elastically upon receipt of a pressing force from opposite sides thereof in a widthwise direction of the ring body, the inner ring presses the outer ring, thus moving the female sexual organ stimulating portion.

As described above, the inner ring deforms elastically upon receipt of the pressing force from the opposite sides thereof in the widthwise direction of the ring body, thus pressing the outer ring and moving the female sexual organ stimulating portion. Thus, during sexual intercourse, it is possible to give a female a feeling of sexual pleasure.

In the invention described in claim 5, there is provided a ring-shaped sexually sensitive portion stimulating tool including an outer ring, approximately U-shaped in section, which has a pair of thick-walled portions whose inner-side surfaces confront each other and a curved portion connecting both thick-walled portions to each other; and an inner ring, approximately U-shaped in section, having a groove open in a peripheral direction thereof. The outer ring is fitted in the groove of the inner ring. Upon receipt of a pressing force applied to an outer-side surface of the inner ring, both tips of the U-shaped inner ring press outer-side surfaces of both thick-walled portions of the outer ring to allow both thick-walled portions to make a rotary motion with an end at the side of the curved portion of an inner-side surface of each of both thick-walled portions of the outer ring operating as a supporting point so that both thick-walled portions stimulate a female sexual organ.

As described above, upon receipt of the pressing force applied to the outer-side surface of the inner ring, both tips of the U-shaped inner ring press the outer-side surfaces of both thick-walled portions of the outer ring to allow each of both thick-walled portions to make a rotary motion with the end at the side of the curved portion of the inner-side surface of both thick-walled portions of the outer ring operating as the supporting point so that both thick-walled portions stimulate the female sexual organ. Therefore, during sexual intercourse it is possible to give a female a feeling of sexual pleasure.

In this case, according to the invention described in claim 6, a positioning member for allowing the outer ring to have a constant distance with respect to the inner ring is provided inside the groove of the inner ring. In this case, even though the outer ring is dislocated from the inner ring in the radial direction of the ring, the outer ring can be immediately returned to the right position with respect to the inner ring.

According to the invention described in claim 7, the positioning member is formed integrally with the outer ring. In this case, the positioning member allows the positional relationship between the outer ring and the inner ring to be proper and allows a cleaning liquid to be sanitary in cleaning the ring-shaped sexually sensitive portion stimulating tool with the cleaning liquid.

In the invention described in claim 8, there is provided a ring-shaped sexually sensitive portion stimulating tool including an outer ring whose outer edge serves as a female sexual organ stimulating portion, and an inner ring whose side surface receives a pressing force. The sexually sensitive portion stimulating tool has a stepped construction in such a way that when the sexually sensitive portion stimulating tool is seen from a peripheral surface side thereof, the inner ring is positioned at an outer side in a widthwise direction of the sexually sensitive portion stimulating tool and the outer ring is positioned at an inner side in the widthwise direction thereof, and the outer ring is positioned outward beyond the inner ring in a radial direction of the sexually sensitive portion stimulating tool to form a stepped construction. The female sexual organ stimulating portion is displaced outward in the widthwise direction of the sexually sensitive portion stimulating tool upon receipt of a pressing force applied to the side surface of the inner ring and stimulates a female sexual organ.

As described above, the female sexual organ stimulating portion displaces outward in the widthwise direction of the sexually sensitive portion stimulating tool upon receipt of the pressing force applied to the side surface of the inner ring and stimulates the female sexual organ. Therefore, during sexual intercourse, it is possible to give a female a feeling of sexual pleasure.

In the invention described in claim 9, the inner diameter of the inner ring is shrunk by a pressing force applied to an outer-side surface of the inner ring to allow the inner ring to squeeze the penis. According to the invention, during sexual intercourse, the erection of the male penis is induced, and an erected state can be maintained.

In the invention described in claim 10, there is provided a ring-shaped sexually sensitive portion stimulating tool, U-shaped in section, including a pair of thick-walled portions whose inner-side surfaces confront each other, and a curved portion connecting both thick-walled portions to each other. Upon receipt of a pressing force applied to an outer-side surface of each of both thick-walled portions, each of both thick-walled portions makes a rotary motion with an end, at the side of the curved portion, of an inner-side surface of each of both thick-walled portions of the outer ring operating as a supporting point and stimulate a female sexual organ.

As described above, upon receipt of the pressing force applied to the outer-side surface of both thick-walled portions, the thick-walled portions makes a rotary motion with the end, at the side of the curved portion, of the inner-side surface of each of both thick-walled portions of the outer ring operating as the supporting point and stimulates the female sexual organ. Therefore, during sexual intercourse, it is possible to give a female a feeling of sexual pleasure.

In this case, according to the invention described in claim 11, both thick-walled portions project inward in such a way that the curved portion is located inward from the thick-walled portions.

According to the invention described in claim 12, a groove for forming an air hole communicating with a space formed of both thick-walled portions, the curved portion and with the outside of each other is formed on an inner-side surface of each of the thick-walled portions. In this case, during sexual intercourse, it is possible to return both thick-walled portions quickly from the outwardly displaced state to the original state and operate both thick-walled portions properly.

According to the invention described in claim 13, a radius is formed on an inner-side end and an outer-side end, in a radial direction of the sexually sensitive portion stimulating tool of a peripheral portion of each of both thick-walled portions in a widthwise direction of the sexually sensitive portion stimulating tool. In this case, during sexual intercourse it is possible prevent a female from having a feeling of physical disorder.

In the invention described in claim 14, there is provided a ring-shaped sexually sensitive portion stimulating tool including a ring body having a first ring portion, a second ring portion parallel with the first ring portion in a widthwise direction of the sexually sensitive portion stimulating tool, and an elastically deformable holding portion for holding the first and second ring portions. The ring body is so formed that the distance between a peripheral portion of the first ring portion and that of the second ring portion in a radial direction of the sexually sensitive portion stimulating tool is varied by a change in a pressing force applied to a side surface of the sexually sensitive portion stimulating tool.

As described above, in the ring body having the first ring portion, the second ring portion, and the holding portion, the ring body is so formed that the distance between the peripheral portion of the first ring portion and that of the second ring portion in the radial direction of the sexually sensitive portion stimulating tool is varied by a change in the pressing force applied to the side surface of the sexually sensitive portion stimulating tool. Thus, the operation of the first ring portion or that of the second ring portion is capable of giving a female a feeling of sexual pleasure during sexual intercourse.

In this case, according to the invention specified in claim 15, the ring-shaped sexually sensitive portion stimulating tool can be constructed so that the holding portion is positioned at an inner peripheral side of the first and second ring portions in the radial direction of the sexually sensitive portion stimulating tool and supports the first and second ring portions at a thin-walled portion thereof thinner than the first and second ring portions, and so that the thin-walled portion supports the first and second ring portions at a side surface thereof opposite to confronting side surfaces of the first and second ring portions.

In the invention described in claim 16, there is provided a ring-shaped sexually sensitive portion stimulating tool which is deformed elastically by a pressing force applied thereto from a side surface thereof in such a way that a female sexual organ stimulating portion formed on a peripheral portion thereof moves and stimulates a female sexual organ.

This construction can also give a feeling of sexual pleasure to a female during a sexual intercourse.

By using a device, for accommodating a sexually sensitive portion stimulating tool according to any one of claims 1 through 16, incorporating a heating/warmth-keeping device for heating the sexually sensitive portion stimulating tool and keeping the sexually sensitive portion stimulating tool warm, it is possible to use the sexually sensitive portion stimulating tool at a moderate temperature.

BEST MODE FOR CARRYING OUT THE INVENTION

The embodiments of the present invention will be described with reference to drawings.
(First Embodiment)

Figure 1:
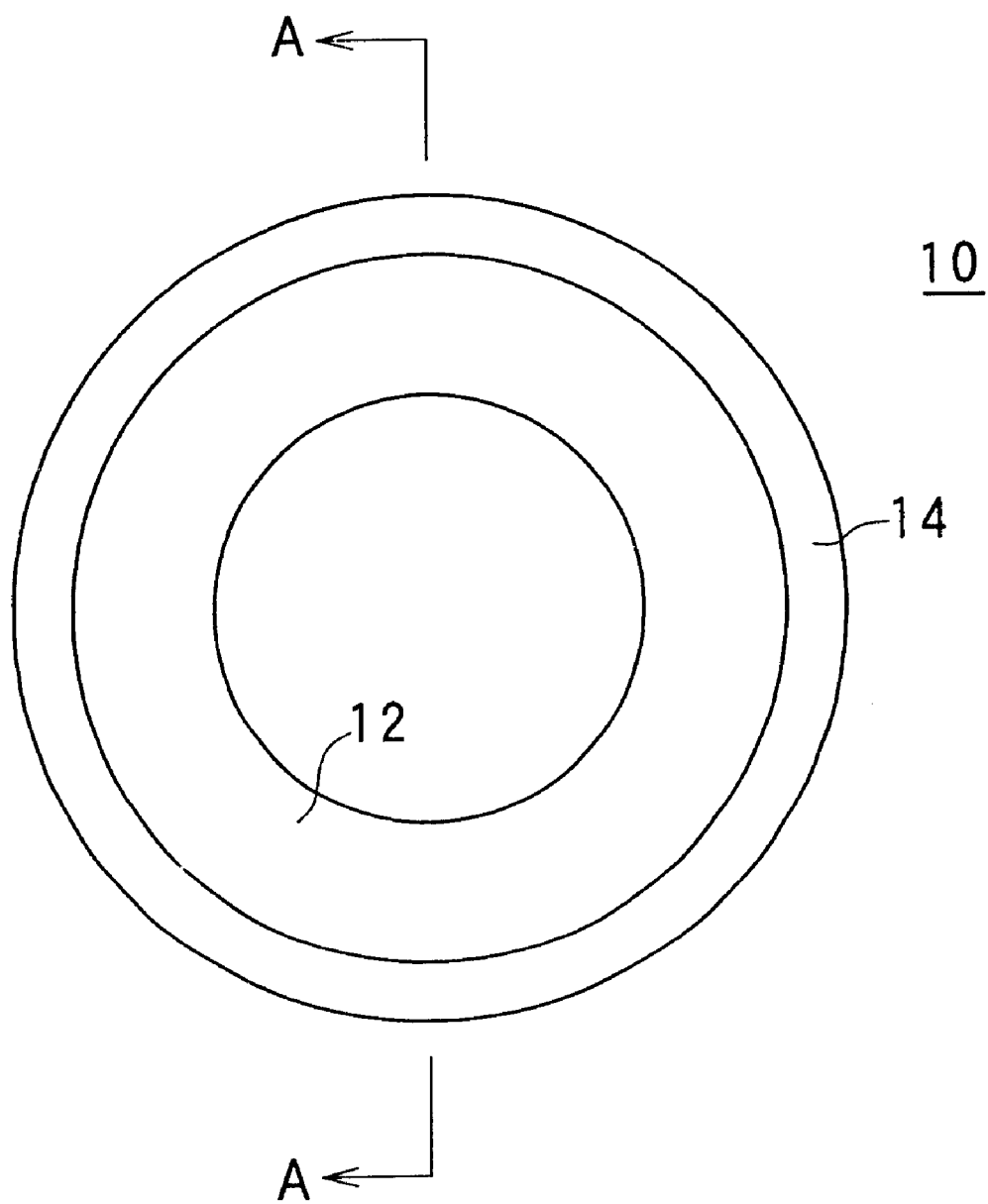
FIG. 1 is a side view of a sexually sensitive portion stimulating ring of an embodiment of the present invention.
Figure 2:
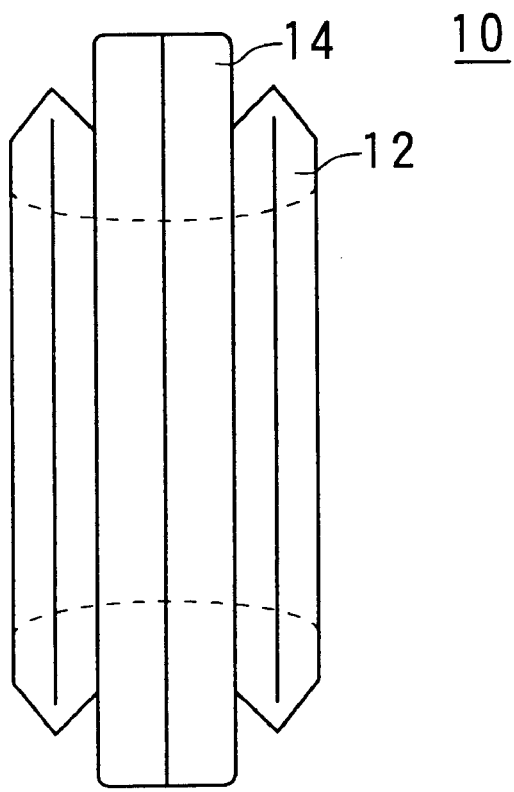
FIG. 2 is a front view of the sexually sensitive portion stimulating ring of the embodiment of the present invention.
Figure 3:
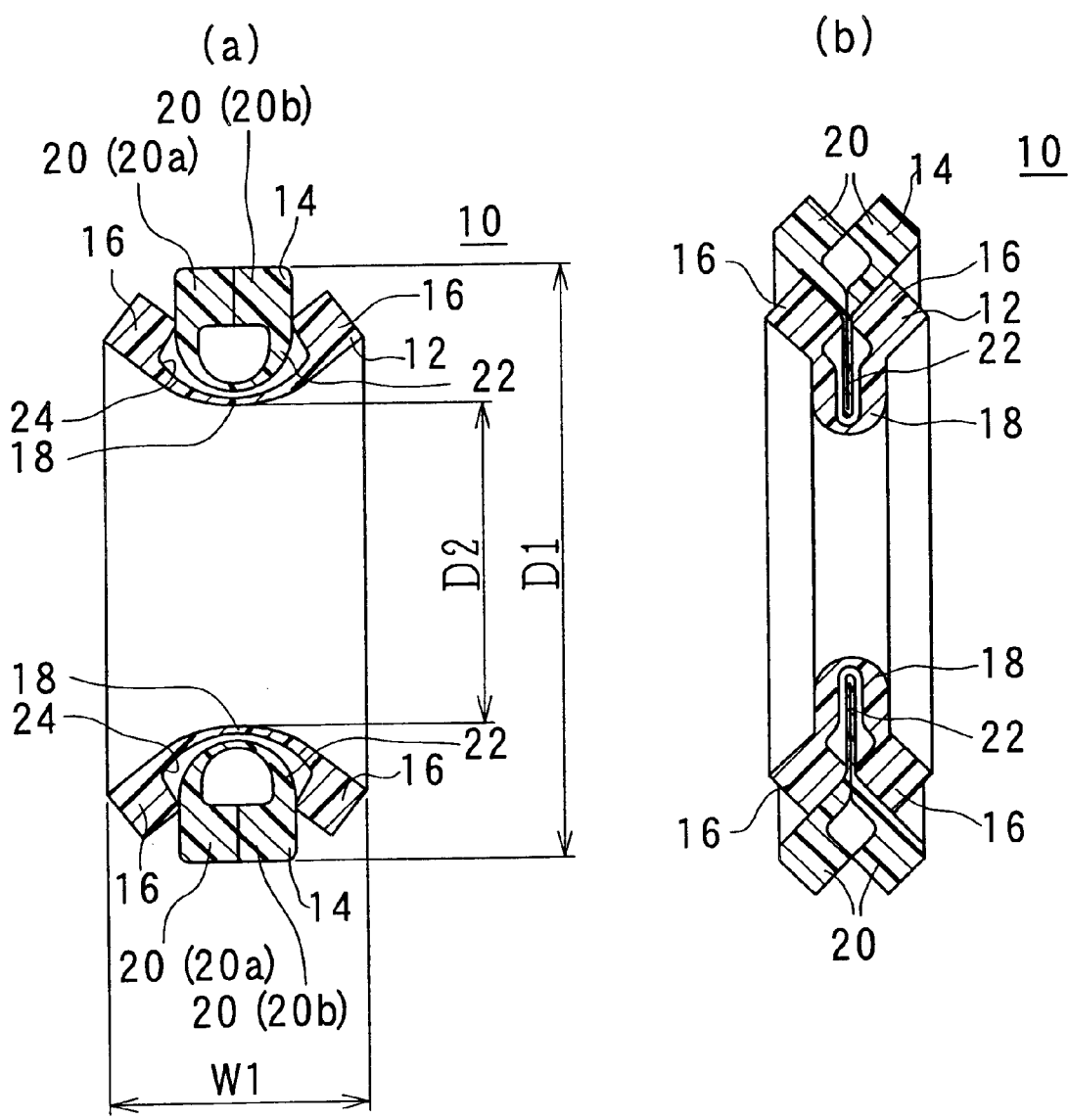
FIG. 3(a) is a sectional view, taken along a line A—A of FIG. 1, of the sexually sensitive portion stimulating ring of the embodiment of the present invention.
FIG. 3(b) is a central cross-sectional view of a state in which the sexually sensitive portion stimulating ring of the embodiment of the present invention is pressed from opposite sides thereof.

FIGS. 1 through 3 show a sexually sensitive portion. stimulating ring serving as a ring-shaped sexually sensitive portion stimulating tool according to an embodiment of the present invention.

FIG. 1 is a side view of the sexually sensitive portion stimulating ring. FIG. 2 is a front view of the sexually sensitive portion stimulating ring. FIG. 3(a) is a sectional view taken along a line A—A of FIG. 1. FIG. 3 (b) is a central cross-sectional view showing a state in which the sexually sensitive portion stimulating ring is pressed from opposite sides thereof.

As shown in FIGS. 1, 2, 3(a), and 3(b), a sexually sensitive portion stimulating ring 10 is constructed by fitting an outer ring 14 serving as a first ring on an inner ring 12 serving as a second ring.

The inner ring 12 is formed annularly from a molded material approximately U-shaped in section. The inner ring 12 is formed in its sectional configuration, as described below. That is, as shown in FIG. 3(a), the inner ring 12 is approximately U-shaped in section and has a concave portion (groove open in peripheral direction) 24 formed inside it. A pair of thick-walled portions (first displacement portion) 16 serving as a female sexual organ stimulating portion are formed at both tips of the approximately U-shaped inner ring 12. The thick-walled portion 16 is formed in the shape of an approximately square and projects inward. A curved portion 18 connecting both thick-walled portions 16 to each other and supporting both thick-walled portions 16 is formed between both thick-walled portions 16.

Similarly to the inner ring 12, the outer ring 14 is annularly formed from a molded material approximately U-shaped in section. The outer ring 14 is formed in its sectional configuration, as described below. That is, as shown in FIG. 3(a), a thick-walled portion (second displacement portion) 20 serving as a female sexual organ stimulating portion and an outer edge portion is formed at both tips of the U-shaped outer ring 14. The thick-walled portion 20 is approximately formed in the shape of a square and projects inward from a side surface of the outer ring 14. A curved portion 22 connecting both thick-walled portions 20 to each other is formed between both thick-walled portions 20. An inner surface of one thick-walled portion 20 and that of the other thick-walled portion 20 contact each other.

The thick-walled portion 20 positioned at the left side of FIG. 3(a) constitutes a first ring portion 20a, whereas the thick-walled portion 20 positioned at the right side constitutes a second ring portion 20b. The inner-side surface of the first ring portion 20a and that of the second ring portion 20b confront each other and are parallel with each other in the widthwise direction (left-to-right direction in FIG. 3(a)) of the ring, namely, the axial direction thereof. The first and second ring portions 20a, 20b are supported by the curved portion 22 serving as a holding portion. The curved portion 22 is positioned at an inner peripheral side (radially inward) of the first and second ring portions 20a, 20b in the radial direction of the ring and constitutes a thin-walled portion thinner than the first and second ring portions 20a, 20b. The curved portion 22 supports the first and second ring portions 20a, 20b at a side surface thereof opposite to the confronting side surface thereof.

The inner diameter of the curved portion 22 of the outer ring 14 is formed a little larger than the inner diameter of the curved portion 18 of the inner ring 12. The outer ring 14 is fitted on the concave portion 24, approximately U-shaped in section and formed on the periphery of the inner ring 12. The thick-walled portion 16 of the inner ring 12 is spread by the outer ring 14, and the corner of the thick-walled portion 16 contacts a boundary portion between the thick-walled portion 20 of the outer ring 14 and the curved portion 22 thereof.

In this manner, an elastically deformable ring body having the outer ring 14 and the inner ring 12 is constructed. As shown in FIG. 2, the sexually sensitive portion stimulating ring 10 has a stepped construction. That is, when the sexually sensitive portion stimulating ring 10 is seen from the peripheral surface side thereof, the inner ring 12 is positioned at the outer side in the widthwise direction of the ring and the outer ring 14 is positioned at the inner side in the widthwise direction thereof, and the outer ring 14 is positioned outward beyond the inner ring 12 in the radial direction (vertical direction in FIG. 2) of the ring.

As shown in FIG. 3(a), in the above-described sexually sensitive portion stimulating ring 10, a diameter D1 thereof is about 70 mm, an inner diameter D2 thereof is about 3 mm, and a width W1 thereof is 23 mm. Both the inner ring 12 and the outer ring 14 are made of high quality silicone rubber, which has a hardness of 15–20° Hs, and are elastically deformable.

The operation of the sexually sensitive portion stimulating ring 10 will be described below.

Figure 4:
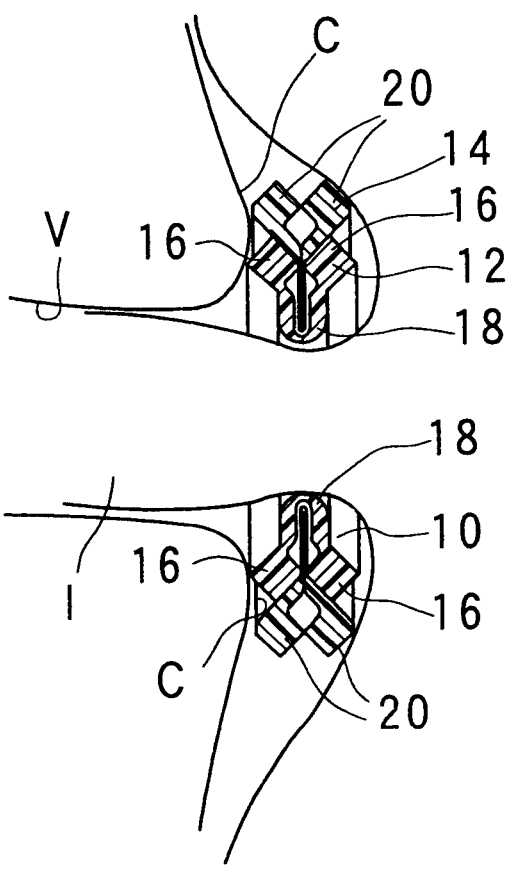
FIG. 4 is a sectional view of a state in which the sexually sensitive portion stimulating ring of the embodiment of the present invention is used.

Initially, as shown in FIG. 4, the sexually sensitive portion stimulating ring 10 is fitted on the root of a penis I. In this state, the sexually sensitive portion stimulating ring 10 has an original shape, as shown in FIG. 3(a).

Then, the penis I is inserted into a vagina V to have a sexual intercourse, with the sexually sensitive portion stimulating ring 10 fitted on the root of the penis I. Thereupon, the side surface of the sexually sensitive portion stimulating ring 10 is pressed by male and female abdomens, with the sexually sensitive portion stimulating ring 10 sandwiched therebetween. Upon receipt of a pressure applied to the inner ring 12 from opposite sides thereof in the widthwise direction of the ring, the inner ring 12 is displaced elastically inward in the widthwise direction of the ring, and the corner of both thick-walled portions 16 of the inner ring 12 presses the boundary portion between the thick-walled portion 20 of the outer ring 14 and the curved portion 22 thereof.

At this time, the thick-walled portion 20 makes a rotary motion with an end, at the side of the curved portion 22, of the inner-side surface of the thick-walled portion 20 of the outer ring 14 operating as the supporting point. That is, the thick-walled portion 20 makes a motion of displacing toward the outer side in the widthwise direction of the ring, while the thick-walled portion 20 is displacing outward in the radial direction of the ring. In other words, the peripheral portion of the thick-walled portion 20 of the outer ring 14 in the radial direction of the ring makes a motion of spreading outward in the widthwise direction of the ring, with the inner peripheral portion of the thick-walled portion 20 in the radial direction of the ring serving as the supporting point. As a result, the thick-walled portion 20 of the outer ring 14 moves (displaces) outward in the widthwise direction of the ring.

As shown in FIG. 3(b), in this state, the thick-walled portion 20 of the outer ring 14 projects outward beyond the thick-walled portion 16 of the inner ring 12, whereas the curved portion 18 of the inner ring 12 flattens and projects inward. The curved portion 22 of the outer ring 14 is surrounded with the curved portion 18 of the inner ring 12. Accordingly, as shown in FIG. 4, the thick-walled portion 20 of the outer ring 14 contacts the female vulva C, and the root of the penis I is squeezed with the curved portion 18. Because the root of the penis I is squeezed, the glans inflates.

As described above, because the inner ring 12 is pressed in the widthwise direction of the ring, the thick-walled portion 16 of the inner ring 12 displaces inward elastically. With the displacement, the thick-walled portion 20 of the outer ring 14 displaces outward in the widthwise direction of the ring. Consequently, there is a change in the distance between the peripheral portion of the first ring portion 20a and that of the second ring portion 20b (between radially outward ends) in the radial direction of the ring.

Accordingly, during sexual intercourse the sexually sensitive portion stimulating ring 10 repeats the following operation: (1) the thick-walled portion 16 of the inner ring 12 contacts the vulva C of the female sexual organ; (2) the thick-walled portion 20 of the outer ring 14 contacts the vulva C of the female sexual organ and the root of the penis I is squeezed by the flattening of the curved portion 18 of the inner ring 12; and (3) the contact of the thick-walled portion 20 of the outer ring 14 with the vulva C of the female sexual organ is released, and the squeezing of the root of the penis I is released by the restoration of the curved portion 18 of the inner ring 12 to the original shape.

Because of the above-described construction, the sexually sensitive portion stimulating ring 10 has the following effect.

During sexual intercourse, because the operation of the above-described (1)–(3) is repeated, the contact of the sexually sensitive portion stimulating ring with the vulva C of the female sexual organ, the separation therefrom, the squeezing of the root of the penis I, and the release of the squeezing thereof are repeated. Accordingly, the erection of the male penis I is induced and an erected state can be maintained. Further, the female vulva C of the female sexual organ is stimulated. Therefore, the female can obtain a feeling of sexual pleasure.

As a result of the motion of the coitus, the sexually sensitive portion stimulating ring 10 repeats the operation of the above-described (1)–(3). Thus, the sexually sensitive portion stimulating ring 10 does not require a power such as a pump and can be used conveniently and safely.

Further, when the penis I is inserted deeply into the vagina V, the sexually sensitive portion stimulating ring 10 is pressed from the opposite sides thereof, and the root of the penis I is squeezed. Thus, the glans of the penis I inflates. Thus, the female can also obtain a feeling of great sexual pleasure.

A more specific embodiment of the sexually sensitive portion stimulating ring 10 will be described below.

Figure 5:
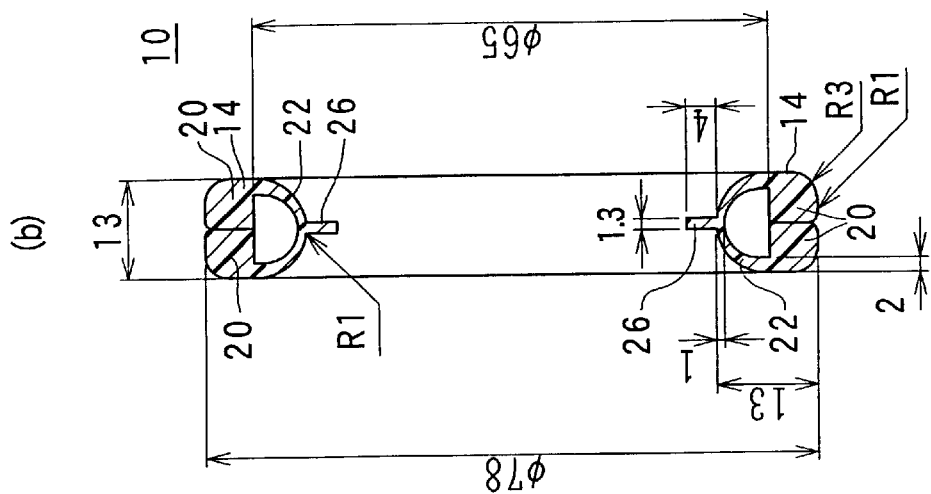
FIGS. 5(a) and 5(b) show the construction of an outer ring in a more specific embodiment of the sexually sensitive portion stimulating ring.
Figure 5:
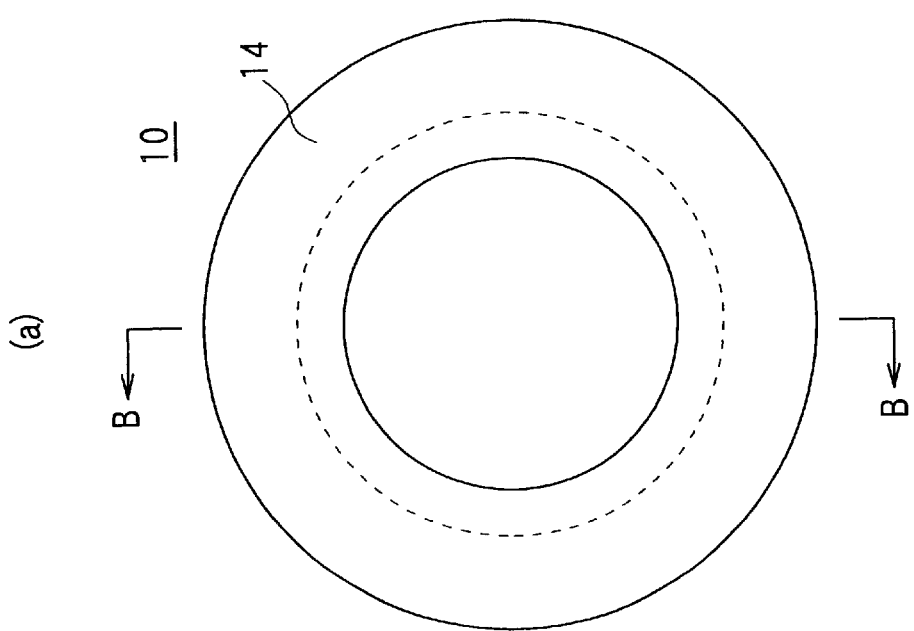
Figure 6:
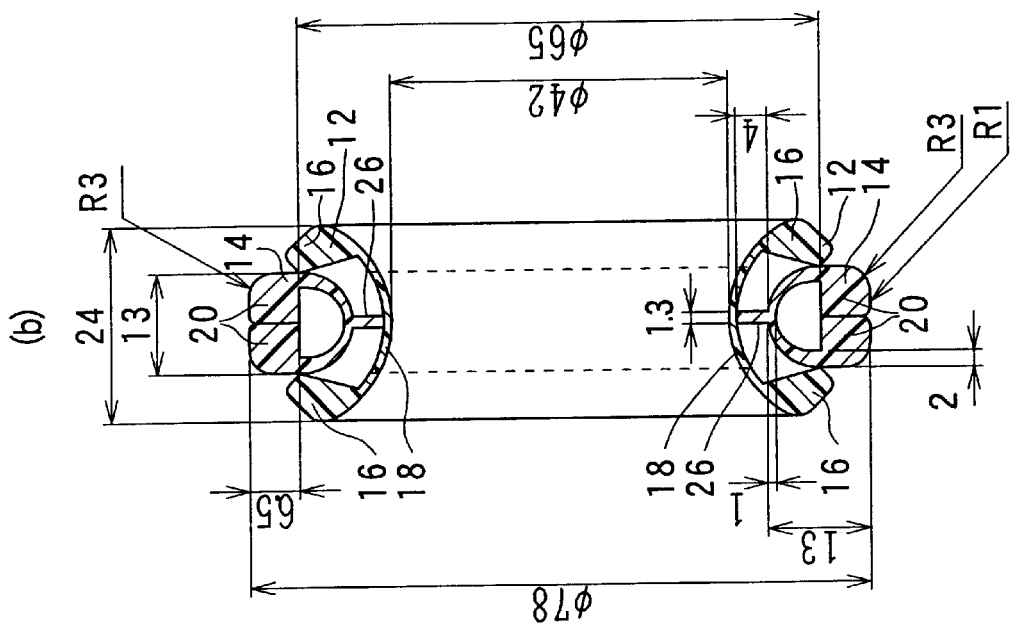
FIG. 6 shows a state in which the outer ring is fitted on an inner ring in the more specific embodiment of the sexually sensitive portion stimulating ring.
Figure 6:
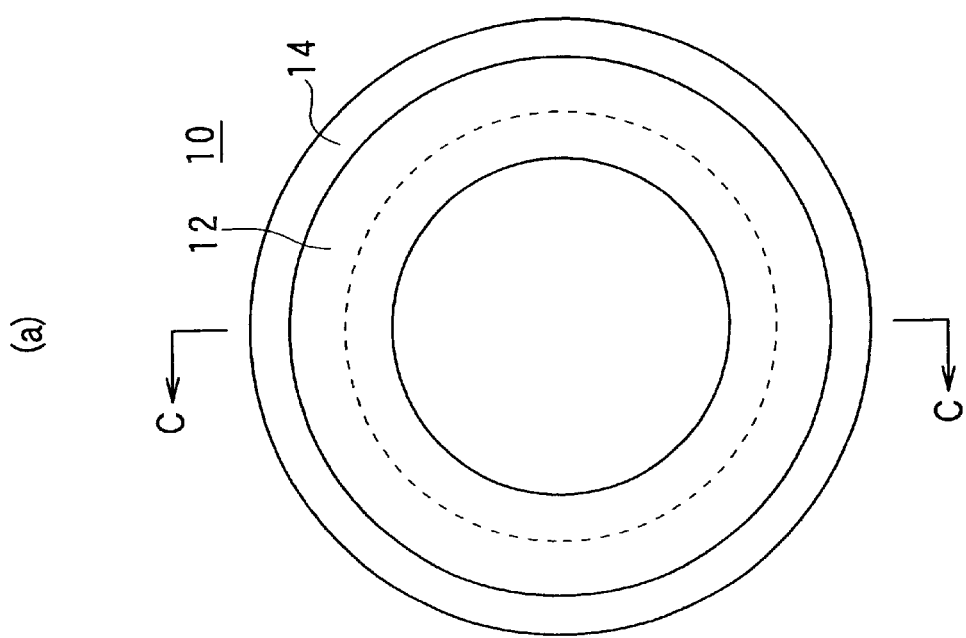

FIG. 5(a) is a side view of the outer ring 14 of the embodiment. FIG. 5(b) is a sectional view taken along a line B—B in FIG. 5(a). FIG. 6(a) is a side view of a state in which the outer ring 14 is fitted on an inner ring 12. FIG. 6(b) is a sectional view taken along a line C—C in FIG. 6(a). FIGS. 5 and 6 show the configuration and numerical values of each portion of the embodiment. The numerical values are indicated with the unit of mm.

In the embodiment, as shown in FIG. 5(b), the outer ring 14 is formed so that a radius is formed on the inner-side end (namely, the end, at the side of the curved portion 22, of the inner-side surface of the thick-walled portion 20 of the outer ring 14) and the outer-side end, in the radial direction of the ring, of the peripheral portion of the thick-walled portion 20 in the widthwise direction of the ring. The thick-walled portion 20 of the outer ring 14 contacts the female vulva C during sexual intercourse. However, if the outer surface of the thick-walled portion 20 of the outer ring 14 is angular, the female has a feeling of physical disorder. Thus, all the corners of the outer surface of the thick-walled portion 20 of the outer ring 14 are rounded in the embodiment, resulting in the prevention of the female having a feeling of physical disorder.

As shown in FIG. 5, a projection 26 is formed integrally with the curved portion 22 of the outer ring 14 such that the projection 26 is disposed on the inner side of the ring in the radial direction thereof. As shown in FIG. 6, with the outer ring 14 fitted on the inner ring 12, the projection 26 operates as a positioning member for allowing the outer ring 14 to have a constant distance with respect to the inner ring 12. That is, if the projection 26 is not formed, during the sexual intercourse, the outer ring 14 remains dislocated from the inner ring 12 in the radial direction of the ring. Consequently, a situation that the thick-walled portion 20 of the outer ring 14 does not operate properly may occur.

Figure 7:
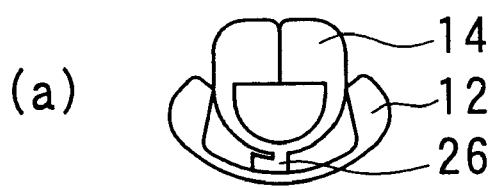
FIG. 7 is an explanatory view for explaining that even though the outer ring of the sexually sensitive portion stimulating ring shown in FIG. 6 is dislocated from the inner ring in a radial direction of the ring, the outer ring can be returned immediately to the right position with respect to the inner ring.
Figure 7:
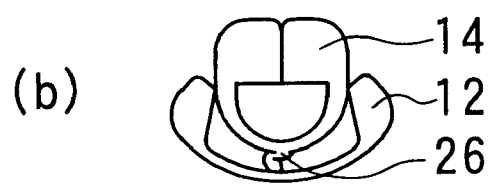
Figure 7:
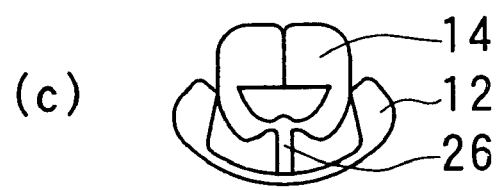

However, by forming the projection 26, even though the outer ring 14 is dislocated from the inner ring 12 in the radial direction of the ring, the outer ring 14 can be returned immediately to the right position with respect to the inner ring 12. That is, as shown in FIG. 7(a), when the outer ring 14 is dislocated from the inner ring 12 in the radial direction of the ring, the projection 26 deforms and operates in a direction in which the deformation is released. Therefore, the state of the projection 26 changes from that shown in FIG. 7(b) to that shown in FIG. 7(c). In this manner, the projection 26 is capable of returning the outer ring 14 to the right position with respect to the inner ring 12.

Figure 8:
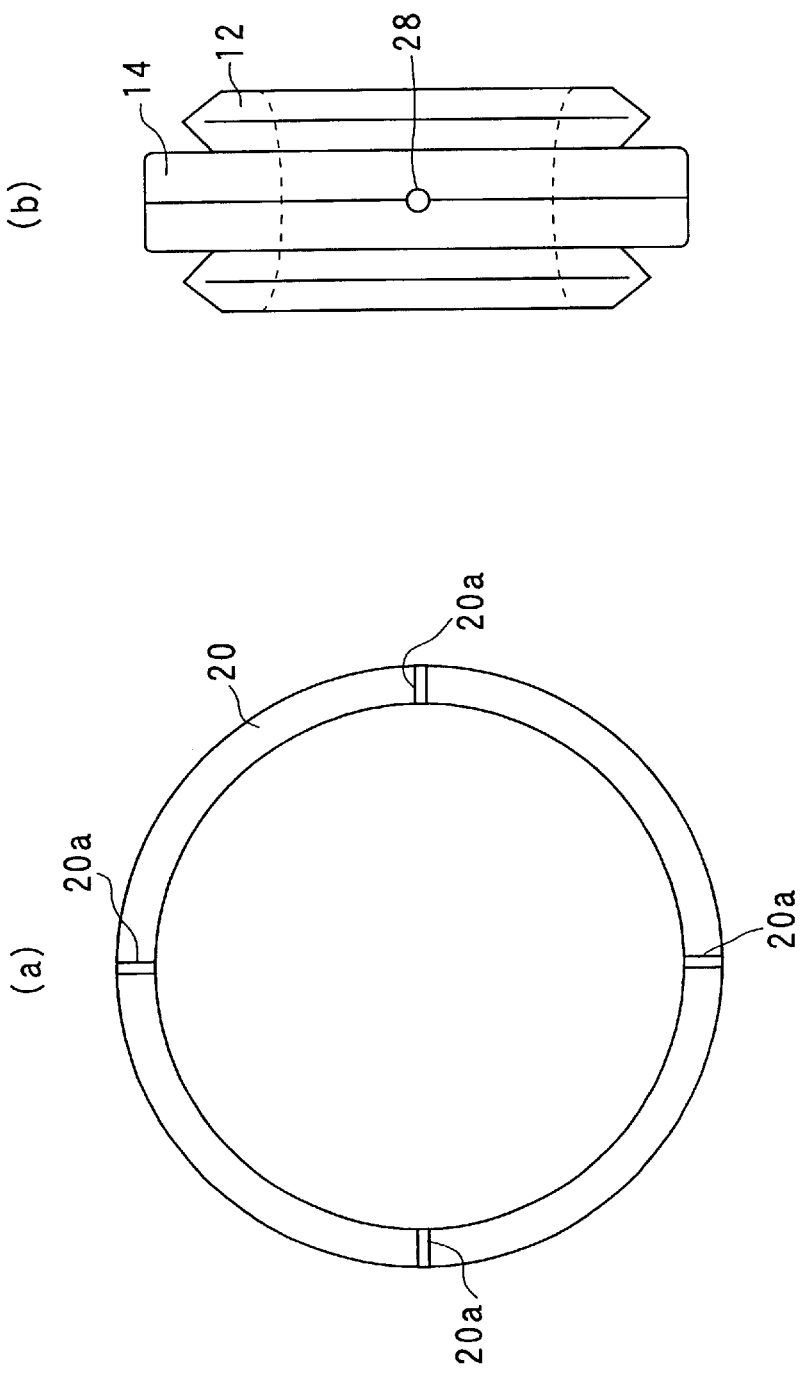
FIGS. 8(a) and 8(b) show a groove formed on an inner-side surface of a thick-walled portion of the outer ring shown in FIGS. 5 and 6 and an air hole formed, with inner-side surfaces of both thick-walled portions in contact each other.

In the embodiment, as shown in FIG. 8(a), a groove 20a is formed on upper, lower, left, and right positions of the inner-side surface of each thick-walled portion 20 of the outer ring 14. With the outer ring 14 fitted on the inner ring 12 and with the inner-side surfaces of both thick-walled portions 20 in contact each other, as shown in FIG. 8(b), the groove 20a allows formation of an air hole 28 communicating with the outside and an inner space formed of thick-walled portions 20 and the curved portion 22 with each other. By forming the air hole 28, during sexual intercourse, it is possible to quickly return both thick-walled portions 20 from the outwardly displaced state to the original state and operate both thick-walled portions 20 properly.

Figure 9:
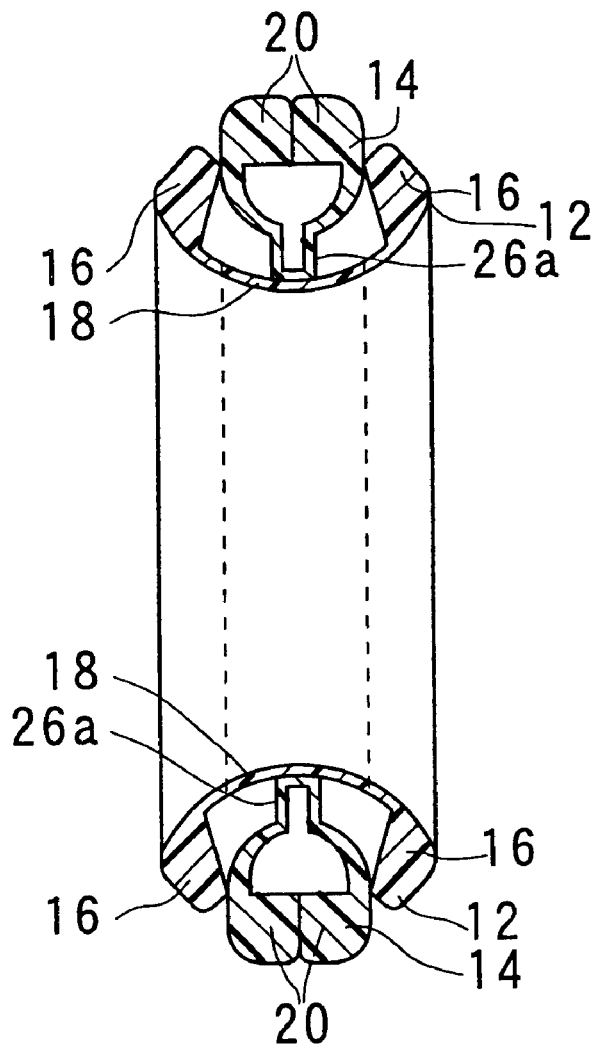
FIG. 9 shows a modification of a projection serving as a positioning member.
Figure 10:
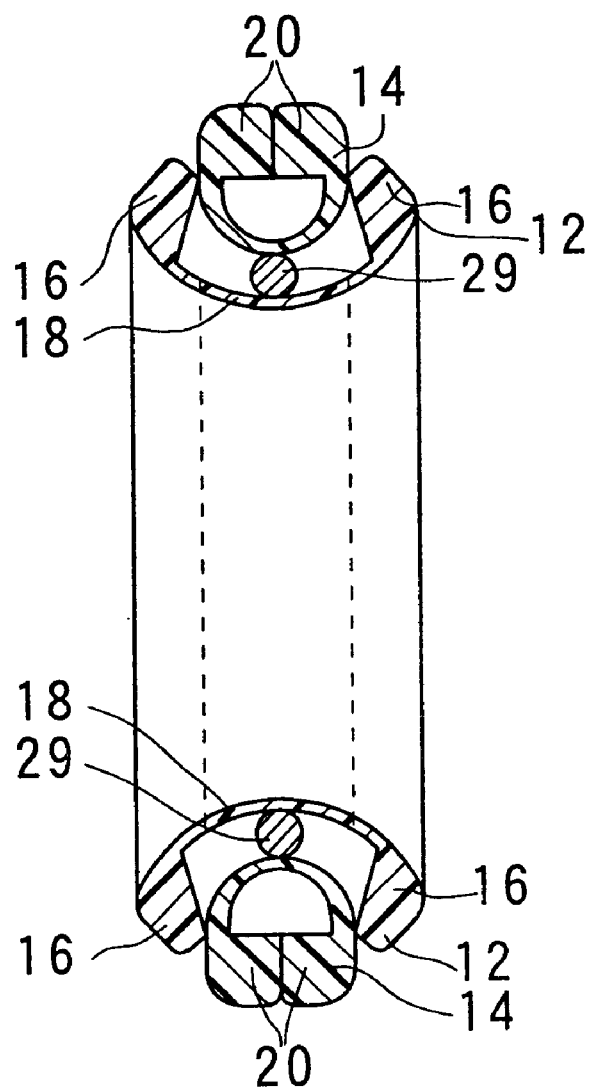
FIG. 10 shows another modification of the positioning member.

In the above-described embodiment, as the positioning member, the projection 26 shown in FIGS. 5 and 6 has been described. But as shown in FIG. 9, a projection 26a having a gap therein may be formed within the positioning member. Because the projection 26 shown in FIGS. 5 and 6 can be manufactured more easily than the projection 26a shown in FIG. 9, the former is more favorable than the latter. Although it is necessary to dispose the projection in the concave portion 24, the projection does not necessarily have to be formed integrally with the outer ring 14. However, in consideration of the above-described positioning operation, it is preferable that the projection is formed integrally with the outer ring 14. The positioning member does not necessarily have to be the above-described projection, but, as shown in FIG. 10, it is possible to use a sectionally circular ring member 29 composed of a material different from that of the outer ring 14. However, in the case where the ring member 29 is composed of a material different from that of the outer ring 14, in washing the sexually sensitive portion stimulating ring 10 with water or the like after it is used, a cleaning liquid may collect between the ring member 29 and the inner ring 12 or the outer ring 14. Therefore, from a sanitary point of view, it is preferable not to compose the ring member 29 of a material different from that of the outer ring 14.

Figure 11:
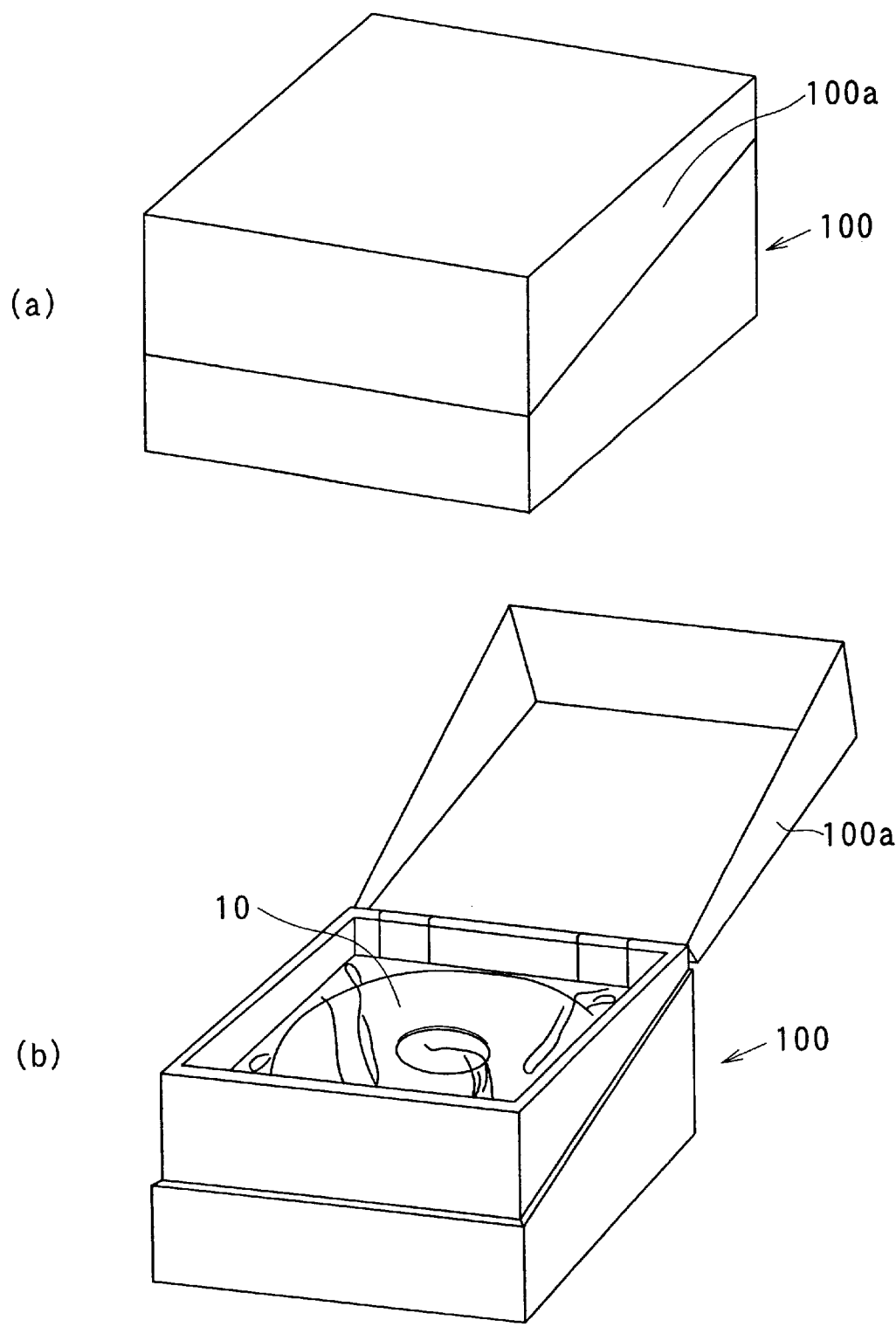
FIG. 11 shows a case for accommodating the sexually sensitive portion stimulating ring.

The above-described sexually sensitive portion stimulating ring 10 is formed by processing silicone rubber of high quality. Prevention measures against static electricity and dust are taken for the sexually sensitive portion stimulating ring 10. But from a sanitary point of view, it is necessary to store it in a case. Therefore, as shown in FIG. 11, the sexually sensitive portion stimulating ring 10 is stored in a case (dressing case) 100 serving as a storing device. FIG. 11(a) shows a state in which a cover 100a of the case 100 is closed. FIG. 11(b) shows a state in which the cover 100a of the case 100 is opened.

Figure 12:
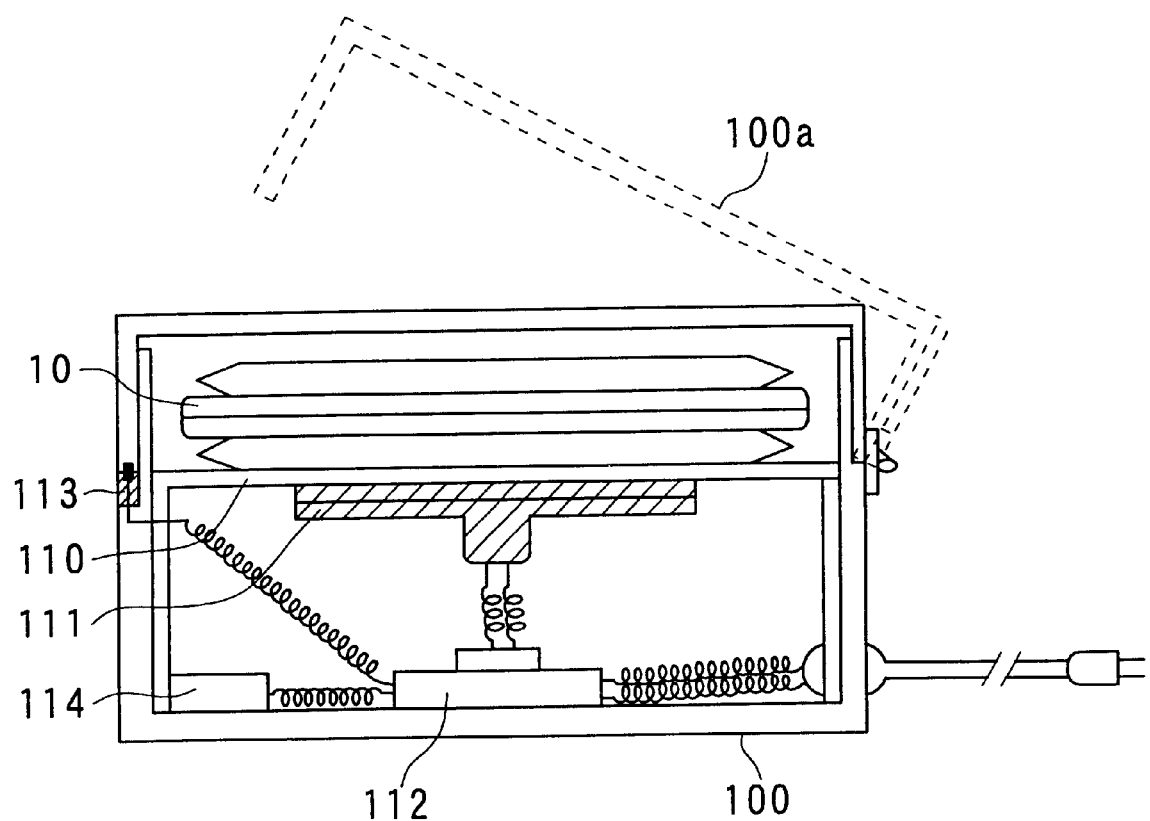
FIG. 12 shows the construction of a heating/warmth-keeping device accommodated in the case shown in FIG. 11.

In using the sexually sensitive portion stimulating ring 10, the female will feel the cold of silicone rubber. Thus it is necessary to keep warming the sexually sensitive portion stimulating ring to body temperature before the sexually sensitive portion stimulating ring 10 is used. Therefore, a heating/warmth-keeping device as shown in FIG. 12 is provided inside the case 100. More specifically, a warming plate 110 is provided inside the case 100. A heater 111 is disposed on the lower surface of the warming plate 110. The sexually sensitive portion stimulating ring 10 is mounted on the upper surface of the warming plate 110. The heating of the heater 111 is controlled by a controller 112. A switch 113 is connected to the controller 112. When the switch 113 is turned on, the controller 112 receives a power supply from a home power source, controls the heating of the heater 111, heats the sexually sensitive portion stimulating ring 10, and keeps warming the sexually sensitive portion stimulating ring 10 to body temperature. When the controller 112 detects that the sexually sensitive portion stimulating ring 10 has reached a predetermined temperature from the heating of the heater 111, it operates a music box 114 to inform a user that the sexually sensitive portion stimulating ring 10 can be used. As the means for informing that the sexually sensitive portion stimulating ring 10 has reached the predetermined temperature, means such as a lamp may be used an addition to, or alternatively to, the music box 114.

A switch for detecting the opening and closing of the cover 110a and a switch for detecting that the sexually sensitive portion stimulating ring 10 is accommodated in the case 100 may be provided so that the heating control of the heater 112 is made based on a signal outputted from the switches only when the controller 112 detects that the sexually sensitive portion stimulating ring 10 is accommodated in the case 100 with the cover 100a open. In this construction, the heating control of the heater 112 can be made only when the sexually sensitive portion stimulating ring 10 can be used.

The present invention is not limited to the above-described embodiment, but can be embodied by altering the above-described embodiment as follows.

(Second Embodiment)

In the above-described embodiment, the ring body having the outer ring 14 and the inner ring 12 separate from the outer ring 14 has been described. But a one-piece ring body may be adopted, so long as the distance between the peripheral portions in the radial direction of the ring is changed by fluctuation of a pressing force applied to the sexually sensitive portion stimulating ring from the side surface thereof.

Figure 13:
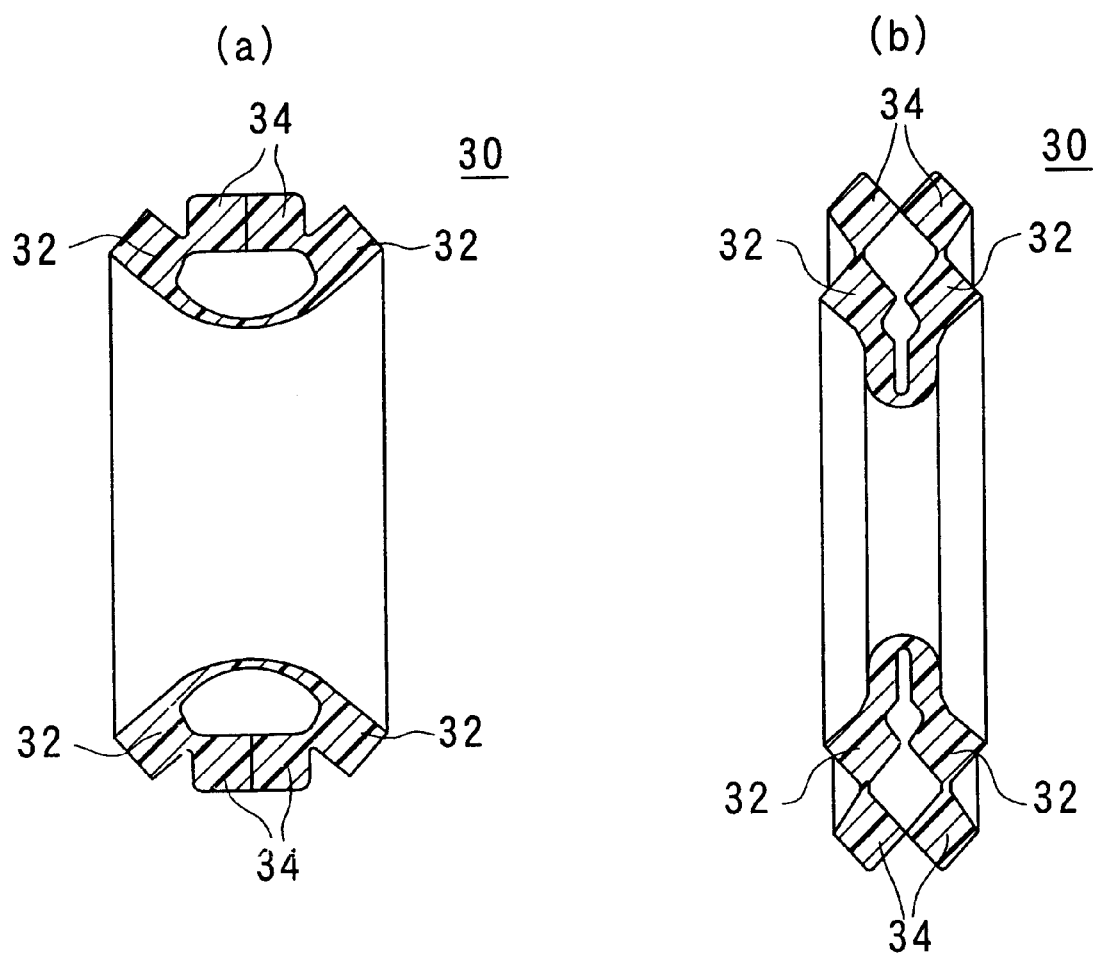
FIG. 13(a) is a central cross-sectional view of the sexually sensitive portion stimulating ring of another embodiment of the present invention.
FIG. 13(b) is a central cross-sectional view of a state in which the sexually sensitive portion stimulating ring of another embodiment of the present invention is pressed from opposite sides thereof.

For example, like a sexually sensitive portion stimulating ring 30 shown in FIGS. 13(a) and (b), in a sectional configuration of the ring, a pair of thick-walled portions 32 are formed at both tips of an inner ring, and a projected portion 34 is extended from the inner side of a pair of the thick-walled portions 32 in such a way that the projected portion 34 is disposed inward from the thick-walled portions 32. In this case, as shown in FIG. 13(b), when the sexually sensitive portion stimulating ring 30 is pressed from the opposite sides thereof, the projected portion 34 is pressed outwardly by a pair of the thick-walled portions 32 and projects outwardly from the thick-walled portions 32. Thus, it is unnecessary to constitute the ring of the outer ring and the inner ring.

According to the second embodiment, the sexually sensitive portion stimulating ring is deformed elastically by a pressing force applied thereto from the side surfaces thereof in such a way that the female sexual organ stimulating portion formed in the peripheral portion of the sexually sensitive portion stimulating ring in its radial direction moves and stimulates the female sexual organ. The sexually sensitive portion stimulating ring is so formed as to have the shape of an approximate "U" in section to form the curved portion as the inner peripheral surface of the sexually sensitive portion stimulating ring. When the sexually sensitive portion stimulating ring is pressed from the opposite sides thereof, the curved portion flattens and the inner diameter of the sexually sensitive portion stimulating ring shrinks. In the U-shaped section of the above-described sexually sensitive portion stimulating ring, a pair of thick-walled portions are formed at both tips of the letter "U", and a pair of the projected portions are extended from the inner side of a pair of the thick-walled portions in such a way that the projected portion is disposed inward from the thick-walled portions. When the sexually sensitive portion stimulating ring is pressed from the opposite sides thereof, the projected portion is pressed outward by a pair of the thick-walled portions and projects outward.

According to the present invention, when the sexually sensitive portion stimulating ring is pressed from the opposite sides thereof, the projected portion is pressed by a pair of the thick-walled portions and projects outward. Thus, during sexual intercourse, the sexually sensitive portion stimulating ring is pressed by the male and female abdomens, with the sexually sensitive portion stimulating ring sandwiched therebetween. As a result, the projected portion is pressed by the thick-walled portion and projects outward. Accordingly, not only the thick-walled portion, but also the projected portion which has projected outwardly contacts the female sexual organ. Because during sexual intercourse the contact of the projected portion with the female sexual organ and separation therefrom are repeated, the female can obtain a feeling of sexual pleasure.

(Third Embodiment)

Figure 14:
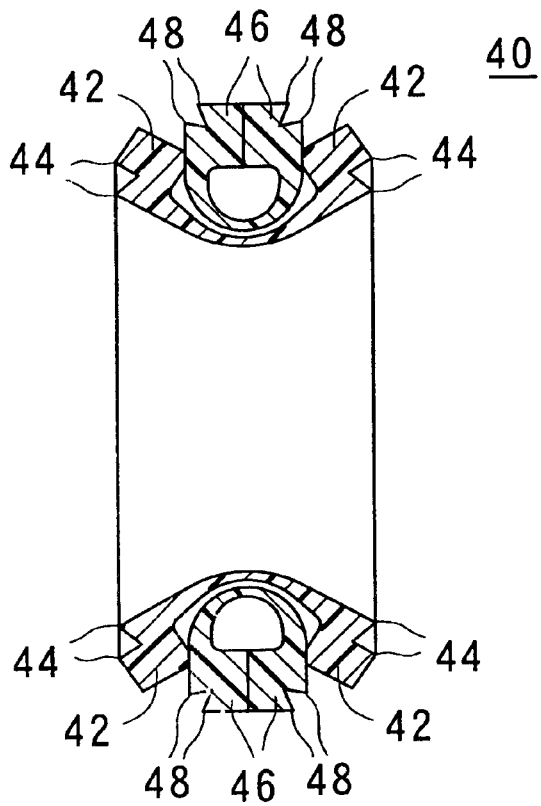
FIG. 14(a) is a central cross-sectional view of the sexually sensitive portion stimulating ring of still another embodiment of the present invention.
FIG. 14(b) is a central cross-sectional view of a state in which the sexually sensitive portion stimulating ring of still another embodiment of the present invention is pressed from opposite sides thereof.
Figure 14:
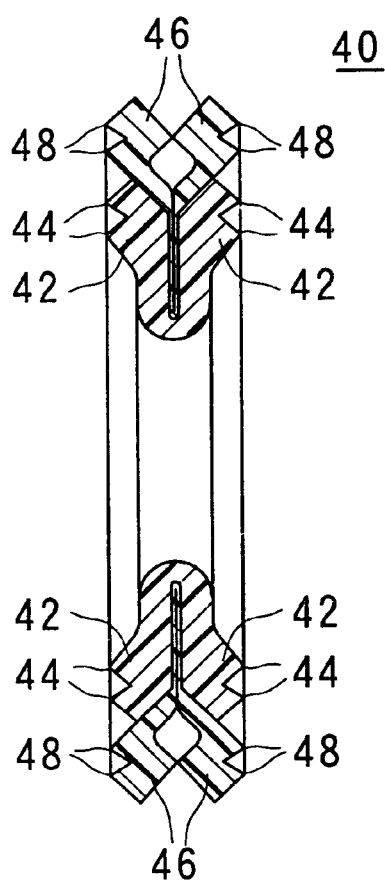

Like a sexually sensitive portion stimulating ring 40 shown in FIGS. 14(*a*) and (*b*), an acute angle portion 44 may be formed on a portion of a thick-walled portion 42 which contacts the female sexual organ, and an acute angle portion 48 may be also formed on a portion of a thick-walled portion 46 which contacts the female sexual organ. In this case, the female sexual organ can be stimulated in a higher extent.

The constructions shown in FIGS. 5 through 10 may be adopted in the second and third embodiments.

In the first through third embodiments, it is possible to prepare a plurality of the sexually sensitive portion stimulating rings having different sizes in the inner diameter of the ring, the outer diameter thereof, and the width thereof. In this case, it is possible to appropriately select a sexually sensitive portion stimulating ring having a suitable size, according to a difference among individuals such as the thickness of the penis.

It is possible to prepare silicone rubber having different levels of hardness. In this case, it is possible to select a desired hardness.

The present invention can be summarized by the followings.

(a) A ring-shaped sexually sensitive portion stimulating ring is fitted on a penis root. The sexually sensitive portion stimulating ring is deformed elastically by a pressing force applied thereto from the side surfaces thereof in such a way that the ring body shrinks in thereof and squeezes the penis and the female sexual organ stimulating portion formed on the periphery of the ring body moves and stimulates the female sexual organ. According to the present invention, the sexually sensitive portion stimulating ring is deformed elastically by the pressing force applied thereto from the side surfaces thereof in such a way that at least the inner diameter of the ring body shrinks and squeezes the penis. Thus, during a sexual intercourse, the erection of the male penis is induced and an erected state can be maintained. Because of the pressing force, the female sexual organ stimulating portion formed on the periphery of the ring body moves and stimulates the female sexual organ. Therefore, during sexual intercourse, the female can also obtain a feeling of sexual pleasure.

(b) In the sexually sensitive portion stimulating ring of the above-described (a), the sexually sensitive portion stimulating ring is formed in the shape of an approximate "U" in section in such a way that the curved portion is formed as the inner peripheral surface of the sexually sensitive portion stimulating ring. When the sexually sensitive portion stimulating ring is pressed from the opposite sides thereof, the curved portion flattens and the inner diameter of the sexually sensitive portion stimulating ring shrinks. According to the present invention, when the sexually sensitive portion stimulating ring is pressed from the opposite sides thereof, the curved portion flattens and the inner diameter of the sexually sensitive portion stimulating ring shrinks. Thus, during sexual intercourse, the sexually sensitive portion stimulating ring is pressed by the male and female abdomens, with the sexually sensitive portion stimulating ring sandwiched therebetween. As a result, the inner diameter of the sexually sensitive portion stimulating ring shrinks. Accordingly, during sexual intercourse, the diameter of the sexually sensitive portion stimulating ring shrinks and expands repeatedly, which induces the erection of the male penis and allows an erected state to be maintained.

(c) In the sexually sensitive portion stimulating ring of the above-described (a) or (b), the inner ring serving as the female sexual organ stimulating portion is formed in the shape of an approximate "U" in section, and the outer ring formed in the shape of an approximate "U" in section is fitted on the inner ring in such a way that when the sexually sensitive portion stimulating ring is pressed from the opposite sides thereof, the outer edge of the outer ring projects outward beyond the inner ring. According to the invention, in addition to the effect of the above-described (b), when the sexually sensitive portion stimulating ring is pressed from the opposite sides thereof, the outer edge of the outer ring projects outward beyond the inner ring. Thus, during sexual intercourse, the sexually sensitive portion stimulating ring is pressed by the male and female abdomens, with the sexually sensitive portion stimulating ring sandwiched therebetween. As a result, the outer edge of the outer ring is pressed outward by the inner ring and projects outward beyond the inner ring. Accordingly, not only the inner ring, but also the outer edge of the outer ring which has projected outward contacts the female sexual organ. During sexual intercourse the contact of the outer edge of the outer ring with the female sexual organ and separation therefrom are repeated, which results in the female obtaining a feeling of sexual pleasure.

What is claimed is:

1. A ring-shaped sexually sensitive portion stimulating tool adapted to be fit on a penis root, comprising:
    an elastically deformable ring body;
    a first displacement portion which is provided on said ring body and is displaced elastically to an inner side in a widthwise direction of said ring body when said ring body is pressed in said widthwise direction of said ring body; and
    a second displacement portion which is provided on said ring body and is displaced to an outer side in said widthwise direction of said ring body with a displacement of said first displacement portion to said inner side in said widthwise direction of said ring body, wherein said second displacement portion is constructed as a female sexual organ stimulating portion.

2. A sexually sensitive portion stimulating tool according to claim 1, wherein said second displacement portion makes a motion of displacing outward in said widthwise direction of said ring body, while said second displacement portion is displacing outward in a radial direction of said ring body.

3. A sexually sensitive portion stimulating tool according to claim 1, wherein a peripheral portion of said second displacement portion makes a motion of spreading outwardly in said widthwise direction of said ring body, with an inner peripheral portion of said second displacement portion in said radial direction of said ring body serving as a supporting point.

4. A ring-shaped sexually sensitive portion stimulating tool adapted to be fit on a penis root, comprising:
   an elastically deformable ring body comprising:
      an inner ring, approximately U-shaped in section, having a groove open in a peripheral direction thereof; and
      an outer ring which has a female sexual organ stimulating portion and which is fitted in said groove of said inner ring,
      wherein when said inner ring deforms elastically upon receipt of a pressing force from opposite sides thereof in a widthwise direction of said ring body, said inner ring presses said outer ring, thus moving said female sexual organ stimulating portion.

5. A ring-shaped sexually sensitive portion stimulating tool adapted to be fit on a penis root, comprising:
   an outer ring, approximately U-shaped in section, having a pair of thick-walled portions whose inner-side surfaces face each other and a curved portion connecting said pair of thick-walled portions to each other; and
   an inner ring, approximately U-shaped in section, having a groove open in a peripheral direction thereof;
   wherein said outer ring is fitted in said groove of said inner ring and upon receipt of a pressing force applied to an outer-side surface of said inner ring, both tips of said U-shaped inner ring press outer-side surfaces of said pair of thick-walled portions of said outer ring to allow each of said pair of thick-walled portions to make a rotary motion, with an end a side of said curved portion operating as a supporting point so that said pair of thick-walled portions is adapted to stimulate a female sexual organ.

6. A sexually sensitive portion stimulating tool according to claim 4, wherein a positioning member for allowing said outer ring to have a constant distance with respect to said inner ring is provided inside said groove of said inner ring.

7. A sexually sensitive portion stimulating tool according to claim 6, wherein said positioning member is formed integrally with said outer ring.

8. A ring-shaped sexually sensitive portion stimulating tool adapted to be fit on a penis root, comprising:
   an outer ring whose outer edge serves as a female sexual organ stimulating portion; and
   an inner ring whose side surface receives a pressing force,
   said sexually sensitive portion stimulating tool having a stepped construction in such a way that when said sexually sensitive portion stimulating tool is seen from a peripheral surface side thereof, said inner ring is positioned at an outer side in a widthwise direction of said sexually sensitive portion stimulating tool and said outer ring is positioned at an inner side in said widthwise direction thereof, and said outer ring is positioned outwardly beyond said inner ring in a radial direction of said sexually sensitive portion stimulating tool to form a stepped construction,
   wherein said female sexual organ stimulating portion displaces outwardly in said widthwise direction of said sexually sensitive portion stimulating tool upon receipt of a pressing force applied to said side surface of said inner ring and is adapted to stimulate a female sexual organ.

9. A sexually sensitive portion stimulating tool according to claim 4, wherein an inner diameter of said inner ring is decreased by a pressing force applied to an outer-side surface of said inner ring to allow said inner ring to squeeze said penis root.

10. A ring shaped sexually sensitive portion stimulating tool adapted to be fit on a penis root and U-shaped in section, comprising:
    a pair of thick-walled portions whose inner-side surfaces face each other; and
    a curved portion connecting said both thick-walled portions to each other,
    wherein upon receipt of a pressing force applied to an outer-side surface of each of said pair of thick-walled portions, said pair of thick-walled portions makes a rotary motion with an end at the side of said curved portion operating as a supporting point for adapting the pair of thick-walled portions to stimulate a female sexual organ.

11. A sexually sensitive portion stimulating tool according to claim 10, wherein said pair of thick-walled portions projects inwardly in such a way that said curved portion is located inwardly from said pair of thick-walled portions.

12. A sexually sensitive portion stimulating tool according to claim 10, wherein a groove for forming an air hole communication with a space formed between said both thick-walled portions and said curved portion and with the outside is formed on an inner-side surface of each of said pair of thick-walled portions.

13. A sexually sensitive portion stimulating tool according to claim 10, wherein a circular configuration is formed by an inner-side end and an outer-side end of each of said pair of thick-walled portions and the curved portion.

14. A ring-shaped sexually sensitive portion stimulating tool adapted to be fit on a penis root, comprising:
    a ring body having a first ring portion; a second ring portion parallel with said first ring portion in a widthwise direction thereof; and an elastically deformable holding portion for holding said first and second ring portions,
    wherein upon receipt of a pressing force applied to a side surface of said ring body, a peripheral portion of each of said first ring portion and said second ring portion in a radial direction of said ring body makes a rotary motion with an inner peripheral side of each of said first ring portion and said second ring portion in said radial direction of said ring body operating as a supporting point for stimulating a female sexual organ.

15. A sexually sensitive portion stimulating tool according to claim 14, wherein said elastically deformable holding portion is positioned at an inner peripheral side of said first and second ring portions in said radial direction of said sexually sensitive portion stimulating tool and supports said first and second ring portions at a thin-walled portion thereof thinner than said first and second ring portions; and said thin-walled portion supports said first and second ring portions at a side surface thereof opposite to confronting side surfaces of said first and second ring portions.

16. A ring shaped sexually sensitive portion stimulating tool adapted to be fit on a penis root and deformed elastically by a pressing force applied thereto from a side surface thereof in such a way that a female sexual organ stimulating portion formed on a peripheral portion thereof is adapted to stimulate a female sexual organ.

17. A sexually sensitive portion stimulating tool according to any one of claims 1 through 16, further comprising a device for accommodating said sexually sensitive portion stimulating tool, said device including a heating/heat-retaining device for heating said sexually sensitive portion stimulating tool.

18. A sexually sensitive portion stimulating tool according to claim 2, wherein a peripheral portion of said second displacement portion makes a motion of spreading outwardly in said widthwise direction of said ring body, with an inner peripheral portion of said second displacement portion in said radial direction of said ring body serving as a support.

19. A sexually sensitive portion stimulating tool according to claim 5, wherein a positioning member for allowing said outer ring to remain a constant distance from said inner ring is provided inside said groove of said inner ring.

20. A sexually sensitive portion stimulating tool according to claim 5, wherein an inner diameter of said inner ring is decreased by a pressing force applied to an outer-side surface of said inner ring for permitting said inner ring to squeeze said penis root.

21. A sexually sensitive portion stimulating tool according to claim 8, wherein an inner diameter of said inner ring is decreased by a pressing force applied to an outer-side surface of said inner ring to allow said inner ring to squeeze said penis root.

22. A sexually sensitive portion stimulating tool according to claim 11, wherein a groove for forming an air hole communicating with a space between said pair of thick-walled portions and said curved portion and with an ambient environment is formed on an inner-side surface of each of said pair of thick-walled portions.

23. A sexually sensitive portion stimulating tool according to any one of claims 18 through 22, further comprising a device for accommodating said sexually sensitive portion stimulating tool, said device including a heating/heat-retaining device for heating said sexually sensitive portion stimulating tool.

* * * * *